(12) United States Patent
Eberle et al.

(10) Patent No.: US 6,526,314 B1
(45) Date of Patent: Feb. 25, 2003

(54) DATA MANAGEMENT SYSTEM FOR IMPLANTABLE CARDIAC DEVICE

(75) Inventors: Jason W. Eberle, St. Louis Park, MN (US); Hiten J. Doshi, Plymouth, MN (US); LeAnne Marie Mackey, St. Louis Park, MN (US); James O. Gilkerson, Stillwater, MN (US); Vickie L. Conley, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/382,034

(22) Filed: Aug. 24, 1999

Related U.S. Application Data

(63) Continuation-in-part of application No. 09/378,317, filed on Aug. 20, 1999.

(51) Int. Cl.$^7$ .............. A61B 5/00; A61B 5/04
(52) U.S. Cl. .............. 600/523; 600/509; 607/9; 607/59
(58) Field of Search .............. 600/509, 523; 607/59, 9

(56) References Cited

U.S. PATENT DOCUMENTS

| | | | |
|---|---|---|---|
| 4,583,553 A | 4/1986 | Shah et al. | 128/704 |
| 4,945,477 A | 7/1990 | Edwards | 364/413.06 |
| 5,007,431 A | 4/1991 | Donehoo, III | 128/696 |
| 5,513,645 A | 5/1996 | Jacobson et al. | 128/710 |
| 5,640,496 A | 6/1997 | Hardy et al. | 395/121 |
| 5,673,031 A | 9/1997 | Meier | 340/825.08 |
| 5,732,708 A | * 3/1998 | Nau et al. | 600/523 |
| 5,859,981 A | 1/1999 | Levin et al. | 395/200.68 |
| 5,908,392 A | 6/1999 | Wilson et al. | 600/509 |
| 5,940,771 A | 8/1999 | Gollnick et al. | 455/517 |
| 5,942,916 A | 8/1999 | Matsbara et al. | 326/83 |
| 6,009,472 A | 12/1999 | Boudou et al. | 709/232 |

FOREIGN PATENT DOCUMENTS

| EP | 0832600 | 9/1997 | A61B/5/00 |
|---|---|---|---|

* cited by examiner

*Primary Examiner*—Carl Layno
(74) *Attorney, Agent, or Firm*—Schwegman, Lundberg, Woessner & Kluth, P.A.

(57) ABSTRACT

A system and method for storing episodic data collected by an implantable medical device. If there are no unallocated storage locations, collected data associated with an episode is stored in locations that are freed from allocations to previous episodes. The least recently allocated of the storage locations allocated to episodes of a lower priority type may be freed first in order to maintain storage of higher priority episodic data. The method and system also allows a specified ratio of stored data allocated to episodes of one priority type to that of another priority type to be maintained.

28 Claims, 3 Drawing Sheets

| | | | |
|---|---|---|---|
| 00 | NULL | 00 | 00 | ← VTR HIGH PRIORITY NODE
| | | 00 | 00 |
| 01 | NULL | 01 | 00 | ← VTR LOW PRIORITY NODE
| | | 01 | 00 |
| 02 | NULL | 02 | 00 | ← ATR NODE
| | | 02 | 00 |
| 03 | NULL | 03 | 00 | ← FREE NODE
| | | 03 | 00 |
| 04 | NULL | 00 | 04 | ← ALL NODE
| | | 00 | 04 |
| 05 | 0X3B | 00 | 00 |
| | | 00 | 0C |
| 06 | 0X1A | 0A | F9 |
| | | 00 | 09 |
| 07 | 0X0E | 00 | 0A |
| | | 03 | 03 |
| 08 | 0X03 | 03 | 07 |
| | | 00 | 0B |
| 09 | 0X02 | 04 | 04 |
| | | 07 | 08 |
| 0A | 0X15 | F9 | 09 |
| | | 02 | 02 |
| 0B | NULL | 00 | 00 |
| | | 00 | 0D |
| 0C | NULL | 00 | 00 |
| | | 00 | 0E |

| IDX | PTR | NEW | NEW ALL |
|---|---|---|---|
| | | OLD | OLD ALL |

| ADDR | LINK | | | DATA |
|---|---|---|---|---|
| 0X00 | NULL | | | |
| 0X01 | 0X06 | | | |
| 0X02 | 0X0D | | | |
| 0X03 | NULL | | | |
| 0X04 | 0X05 | | | XX |
| 0X05 | 0X09 | | | XX |
| 0X06 | 0X0A | | | |
| 0X07 | 0X08 | | | |
| 0X08 | NULL | | | |
| 0X09 | 0X0C | | | XX |
| 0X0A | 0X0B | | | |
| 0X0B | NULL | | | |
| 0X0C | 0X0F | | | XX |
| 0X0D | NULL | | | |
| 0X0E | NULL | | | |
| 0X0F | 0X10 | | | XX |
| 0X10 | 0X13 | | | XX |
| 0X11 | 0X07 | | | |
| 0X12 | NULL | | | |
| 0X13 | 0X14 | | | XX |
| 0X14 | 0X16 | | | XX |
| 0X15 | NULL | | | |
| 0X16 | 0X17 | | | XX |
| 0X17 | 0X19 | | | XX |
| 0X18 | 0X12 | | | |
| 0X19 | 0X1B | | | XX |
| 0X1A | 0X00 | | | |
| 0X1B | 0X1C | | | XX |

FREE PTR → (at 0X04)
~20

DATA MANAGEMENT SYSTEM FOR IMPLANTABLE CARDIAC DEVICE

CROSS REFERENCE TO RELATED APPLICATIONS

This application is a continuation-in-part of U.S. patent application Ser. No. 09/378,317, filed on Aug. 20, 1999, the specification of which is incorporated herein by reference.

FIELD OF THE INVENTION

This invention pertains to implantable medical devices, such as cardiac pacemakers and implantable cardioverter/defibrillators, with data gathering capabilities. In particular, the invention relates to systems and methods for managing the storage and retrieval of episodic information gathered during operation of the device.

BACKGROUND

Implantable medical devices, such as cardiac pacemakers and implantable cardioverter/defibrillators have a limited amount of memory for storing data associated with episodes and therapy attempts. Previous methods of data storage have used a simple first-in, first-out rule for storing the data associated with episodes and therapy attempts with the assumption that there is enough memory so all data of interest can be retrieved before it is overwritten by newer data. Previous devices have also partitioned the data by type (electrogram data, interval data, episode and attempt data) where the first-in, first-out rule is applied individually to each type of data.

Although newer devices have increased the amount of memory available for storage, the assumption that data not yet retrieved still exists in device memory may still not hold true in many cases. For example, electrogram data almost always get overwritten first because a smaller amount of storage is available for electrogram data relative to the amounts dedicated to interval data and episode data. There are also cases where a patient has recurring arrhythmias of a certain type which overwrite the data from the infrequent arrhythmias which are of real interest to the physician. Newer devices are expanding the scope of arrhythmias that can be treated and consequently more data is generated for the newer types of arrhythmias. This leads to a need to manage the data storage such that the data of most interest is preserved.

SUMMARY OF THE INVENTION

The present invention is a system and method for storing episodic data collected by an implantable medical device. In one embodiment, previously used data storage locations are freed for overwriting with new data in accordance with a priority protection scheme. A data storage segmentation scheme may also be used that attempts to maintain a specified ratio of types stored data if unallocated storage space is unavailable.

In a particular implementation of the invention, collected data associated with an episode is stored in data storage locations referenced by storage nodes, where an episode is defined as any detected condition requiring the recordation of data. A linked list of unallocated storage nodes is maintained so that a storage node from the unallocated list can be allocated to each episode for which collected data is to be stored. In addition, a priority type linked list corresponding to each one of a plurality of episode priority types is also maintained, wherein each priority type linked list comprises storage nodes allocated to episodes of a particular type linked in an order that corresponds to when the episodes occurred. When the unallocated list of storage nodes is empty, storage nodes are freed for allocation to a present episode by freeing the oldest data storage node from one of the priority type lists, wherein the freed node is taken from a lower priority list in preference to a higher priority list. In accordance with a data storage segmentation scheme, storage nodes may be freed from priority type lists and allocated to new episodes in a manner that attempts to maintain the number of stored episodes of a particular type below a specified maximum number.

The storage nodes may reference a plurality of locations for storing a plurality of types of data associated with the episode. In a specific embodiment, data storage locations may be allocated to therapy attempts associated with an episode, and data collected prior to onset of the episode may be stored in a location referenced by the data storage node allocated to the episode. In a further specific embodiment, data collected before and after the therapy attempt may be stored in locations referenced by the data storage node allocated to the attempt.

BRIEF DESCRIPTION OF THE DRAWINGS

FIG. 1A is a representation of the history management structure.

FIG. 1B depicts the fields of a single node of the history management structure.

DETAILED DESCRIPTION OF THE INVENTION

Figures 2A, 2B:
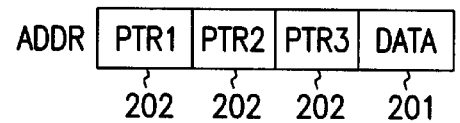
FIG. 2A is a representation of the history storage structure.
FIG. 2B depicts the fields of a history storage node.

As aforesaid, the present invention is a method and system for storing episodic data collected by an implantable medical device. An "episode" may be defined as any condition detected by the device via its sensing channels that requires the recordation of data. An episode may be, for example, a clinically significant condition occurring in a patient for which data recorded immediately prior to, during, and/or after the onset of the episode constitutes useful information for the treating clinician when the data is retrieved from the device with a programmer or similar telemetry device. Another type of episodic data is data collected before and after any therapy attempts performed by the device after detection of the onset of an episode requiring such therapy. For example, in an implantable cardioverter/defibrillator (ICD), a detected cardiac anlhythmia may constitute an episode, and any cardioversion/defibrillation shocks delivered to the heart in response to the arrhythmia would constitute therapy attempts associated with the episode. Similarly, in a pacemaker, a bradycardic or tachycardic arrhythmia could be an episode requiring the recordation of data, and any pacing therapy delivered in response would be a therapy attempt associated with the episode.

Data may be collected by an implantable medical device that incorporates the present invention via sensing channels that sense physiological variables. In a pacemaker/ICD device, sensing channels comprise electrodes and amplifiers for sensing cardiac electrical activity. The sensing channel signals may then be msed to derive an electrogram, which is time referenced recording of cardiac electrical activity from the location of the electrode. (Electrograms are thus analogous to the familiar electrocardiogram or EKG which is obtained from external electrodes on the body surface.) Sensing channel signals may also be used to derive interval data which is a time referenced recording of the time intervals between cardiac events such as depolarizations and repolarizations occurring in the atria or ventricles. In certain devices, data may be continually stored in a circular input buffer as it is collected with the oldest data in the buffer being continually overwritten. Episodic data can be stored by transferring the data in the input buffer to a more permanent location after onset of an episode (or therapy attempt) and for a specified time thereafter. The continual storage of data before onset of the episode (or therapy attempt) also allows pre-episode (or pre-attempt) data to be stored and associated with the episode (or attempt).

In one specific embodiment, a data storage system in accordance with the invention comprises a number of interrelated data structures. A history storage structure comprising an array of nodes (wherein the terms "nodes" and "elements" are synonymous as used herein) used to reference data storage locations. In order to store data associated with an episode, a history storage node is allocated to the episode. The history storage node allocated to a new episode is taken from a linked list of unallocated history storage nodes if possible (i.e., if the list is not empty), else the node is allocated from a list of previously allocated history storage nodes. The system further includes a priority type linked list of previously allocated history storage nodes for each one of a plurality of types of episodes. Episodes are classified as being one of a plurality of priority types going from lower to higher, where a higher priority episode would be one regarded as more significant or of greater interest so it should be preferentially retained in storage. When a history storage node is allocated to an episode, the node is placed in a priority type linked list in accordance with the type of episode to which the node has been allocated. The history storage node may have a data field that indicates whether the node has been allocated to an episode or is free. The system may also include a priority protection scheme so that when a previously allocated node must be allocated to a new episode, the oldest node from one of the priority type lists is freed for allocation to the new episode, with the freed node taken from a lower priority list in preference to a higher priority list. A data storage segmentation scheme may be also be employed such that nodes are freed from priority type lists and allocated to new episodes in a manner such that a spbcified maximum number of stored episodes of one particular type will not be exceeded.

A further refinement in the system may be had by including a history management structure comprising an array of nodes, such that for each history storage node allocated to an episode, a history management node is also allocated to the episode and associated with the allocated history storage node. Each allocated history management node has a storage link field that points to the history storage node associated therewith. The priority type linked lists of history storage nodes may then be formed by linking associated history management nodes, where each allocated history management node has a link field pointing to an adjacent node in a priority type linked list of history management nodes. The priority type linked lists may be doubly linked lists with each allocated history management node having link fields pointing to adjacent nodes in both directions, which then allows insertions and deletions to be made at arbitrary points within the list without a list traversal. Another linked list that may be included is a doubly linked list of all allocated history management nodes, with each allocated node having link fields pointing to adjacent nodes in both directions in the all allocated node list. The nodes of the priority type linked lists and the all allocated linked list are linked sequentially in accordance with when the episodes to which the nodes are allocated occurred. Both the all allocated list and the priority type lists thus constitute a sequence of episodes for which data has been collected in the order in which the episodes occurred.

The system may further include a data storage structure comprising an array of nodes, where for each history storage and history management node allocated to an episode, a data storage node is also allocated to the episode and associated with the allocated history storage and history management node. Each allocated history storage node has a link field pointing to an associated data storage node, and each data storage node references a data storage block in which episodic data is actually stored. Episodic data may be stored in a plurality of data storage blocks referenced by a linked list of data storage nodes allocated to the episode with each allocated data storage node having a link field for pointing to an adjacent data storage node in the linked list.

The history management structure may be further modified to include nodes designated as list heads for the unallocated linked list, the all allocated linked list, and the priority type linked lists. In order to facilitate additions and deletions to all the lists, they may be made doubly linked with each history management node designated as a list head having link fields for pointing to adjacent nodes in both directions. (A "list head" is a special identifiable node in a circularly linked list.)

The system may also allow for the recordation of data related to therapy attempts delivered by the device. Episodic data collected before and after a therapy attempt associated with an episode may be stored in a plurality of data storage blocks referenced by a linked list of data storage nodes allocated to storing data collected before and after the attempt. In order to link attempt data to the episode with which the data is associated, a history storage node allocated to an episode has a link field that may reference a history storage node allocated to a therapy attempt associated with the episode. A history storage node allocated to an attempt has a data field in which is stored a value indicating that the node is allocated to an attempt, a link field that references a data storage node allocated to storing data collected before the therapy attempt, and a link field that references a data storage node allocated to storing data collected after the therapy attempt. The history storage node allocated to an attempt further has a link field that may reference history storage nodes allocated to any subsequent attempts.

A history storage node may be allocated to a new therapy attempt associated with an episode from the list of unallocated history storage nodes unless the unallocated list is empty, in which case the oldest node from one of the priority type lists is freed and added to the unallocated list for allocation to the new episode. The freed node is taken from a lower priority list in preference to a higher priority list in order to provide priority protection. In order to provide data storage segmentation, nodes are freed from priority type lists and allocated to new episodes in a manner such that a specified maximum number of stored episodes of one particular type will not be exceeded. Priority protection and data storage segmentation may also be combined. Data storage nodes (and the data storage blocks to which they refer) may be allocated in a similar manner.

As described above, the system allocates history storage nodes and history management nodes by freeing the nodes from one of the priority lists when the unallocated list is empty. When a history storage node allocated to an episode is freed, the history management node allocated to the episode, all history storage nodes allocated to therapy attempts associated with the episode, and all data storage nodes and blocks allocated to the episode or associated attempts are also freed.

The following description is of a particular embodiment of the invention as implemented in an implantable cardiac device having the capability of collecting data by sensing cardiac intervals and electrograms, and further having the capability of delivering electrical therapy to the heart. The data storage system to be described is implemented in software in a microprocessor-based device and stores data associated with specific detected episodes. Episodes may be defined as a defined set of collected data that corresponds to a type of cardiac arrhythmia that either requires delivery of electrical therapy or is clinically significant enough to require recording of the data.

The system uses a priority protection scheme that preserves episode data with certain types of arrhythmias. Episodes are classified high or low priority based on pre-defined criteria. High priority episodes are only overwritten if all space available for storing data is occupied by previous high priority episodes. The system also employs a data storage segmentation scheme that allows storage of both atrial tachyarrhythmia response (ATR) and ventricular tachyarrhythmia response (VTR) episode detail, interval data, and electrogram data in memory, while restricting the amount of space given to each type within a programmable limit. The storage segmentation can be reprogrammed at any time without losing any stored data. When the storage segmentation is changed, new episode data of one type will overwrite episode data of the other type until the proper data storage segmentation is once again established.

Three types of history data are maintained: episode and attempt data, interval data, and electrogram data. Episode and attempt data are maintained in the history storage structure. Interval data is maintained in the interval data storage structure, and electrogram data is maintained in the electrogram data storage structure. A fourth structure, the history management structure 10 is shown in FIG. 1A, and is used to track the chronological order of the episodes. This structure tracks the order of all episodes stored in memory, as well as the order of the individual classifications of episodes (ATR, VTR high priority, and VTR low priority). The history management structure is the starting point for accessing history data.

The history management structure is a constant sized array of elemsents or nodes used to keep track of all episodes stored in memory. Each element 100 is itself a data structure containing five indices as shown in FIG. 2B:

1) the history storage location index 101, which is an index into the history storage structure described below and points to the history storage node allocated to the episode;
2) the newer episode index 102 in the list of all episodes (i.e., the all allocated list of nodes);
3) the older episode index 103 in the list of all episodes;
4) the newer episode index 104 in the list of all episodes of the same classification (i.e., the priority type list to which the node has been assigned); and,
5) the older episode index 105 in the list of all episodes of the same classification.

(The terms index, pointer, link, or reference as used herein denotes a mechanism for accessing a specific memory location.)

Episodes and attempts are stored in the history storage structure 20 represented in FIG. 2A. Each node 200 of the history storage structure is made up of two components, the data field 201 and the link fields 202. FIG. 2B depicts the components of a history storage node. The data component 201 of the history storage element identifies how the element is allocated and can either contain episode data, attempt data, or no data if the node is free. If the data is episode data, it can be a ventricular tachyarrhythmia response episode or an atrial tachyarrhythmia response episode. The link fields 202 of the node vary according to whether the node is allocated to an episode, an attempt or is free as indicated by the type of data currently in the data field 201. If the data field of the node contains episode data, the link fields contain the index of the first attempt node in the episode (i.e., the first history storage node allocated to a therapy attempt associated with the episode), the index of the first segment of interval data for the episode, and the index of the first segment of electrogram data for the onset electrogram strip. If the data field of the node contains attempt data, the link fields contain the index of the next attempt node in the episode, the index of the first segment of pre-attempt electrogram data for the attempt, and the index of the first segment of post-attempt electrogram data for the attempt. If the history storage node is free, the link field contains the index of the next free history storage node in a linked list of all free history storage nodes.

Interval data is segmented into constant sized data storage blocks. Multiple blocks are linked together to store the interval data for a single episode. These blocks are referenced by an index that identifies the location of the data storage block in memory and also identifies a corresponding node of an interval data storage structure. The sequence of the stored interval data is maintained within the data storage structure as a linked list of data storage nodes, where each node of the data storage structure has a link field that points to the corresponding data storage node of the next interval data storage block in the storage sequence.

Electrogram data is also segmented into constant sized data storage blocks. Multiple blocks are linked together to store the electrogram data for a single electrogram strip. These blocks are referenced by an index that identifies the location of the data storage block in memory and also identifies a corresponding node of an electrogram data storage structure. The sequence of the stored electrogram data is maintained within the data storage structure as a linked list of data storage nodes, where each node of the data storage structure has a link field that points to the corresponding data storage node of the next electrogram data storage block in the storage sequence.

At initialization, the history management nodes are placed in a doubly linked list. There are five reserved nodes in the history management structure that serve as list heads for five doubly linked lists of history management nodes. The first node is the unallocated list head which is used to access a linked list of those history management nodes that are not currently being used to track episode data. Initially, all nodes in the structure are linked to the unallocated list head. The second reserved node is the all allocated list head. The all allocated list head maintains the linked list of all episodes currently stored in memory, in the order in which they occurred. The other three reserved nodes are list heads used to track ATR episodes, VTR high priority episodes, and VTR low priority episodes. Each of these individual linked lists contains the episodes of that classification in the order which they occurred. Every stored episode is accounted for in one of these three lists, and in the all allocated list.

The unallocated history storage nodes are initially placed in a singly linked list, with the first free node pointed to by a storage node free pointer. Similarly, the unallocated interval data storage nodes are placed in a singly linked list pointed to by the interval data storage free pointer, and the electrogram data storage nodes are placed in a singly linked list pointed to by the electrogram data storage free pointer.

When an episode occurs, a new history storage node must be allocated. If there is a history storage node in the unallocated list, that node is used for the new episode. In a similar fashion, a history management node is taken from the unallocated list as pointed to by the unallocated list head node. The system is designed such that the number of history storage nodes in use is always greater than or equal to the number of history management nodes in use. This is because the history storage structure contains nodes allocated to both episodes and attempts, while the history management structure contains only nodes allocated to episodes. Any therapy attempts recorded during a VTR episode also requires the use of a history storage node. A free history storage node for an attempt is obtained using the same logic as was used to obtain a history storage node for the episode.

Figure 3:
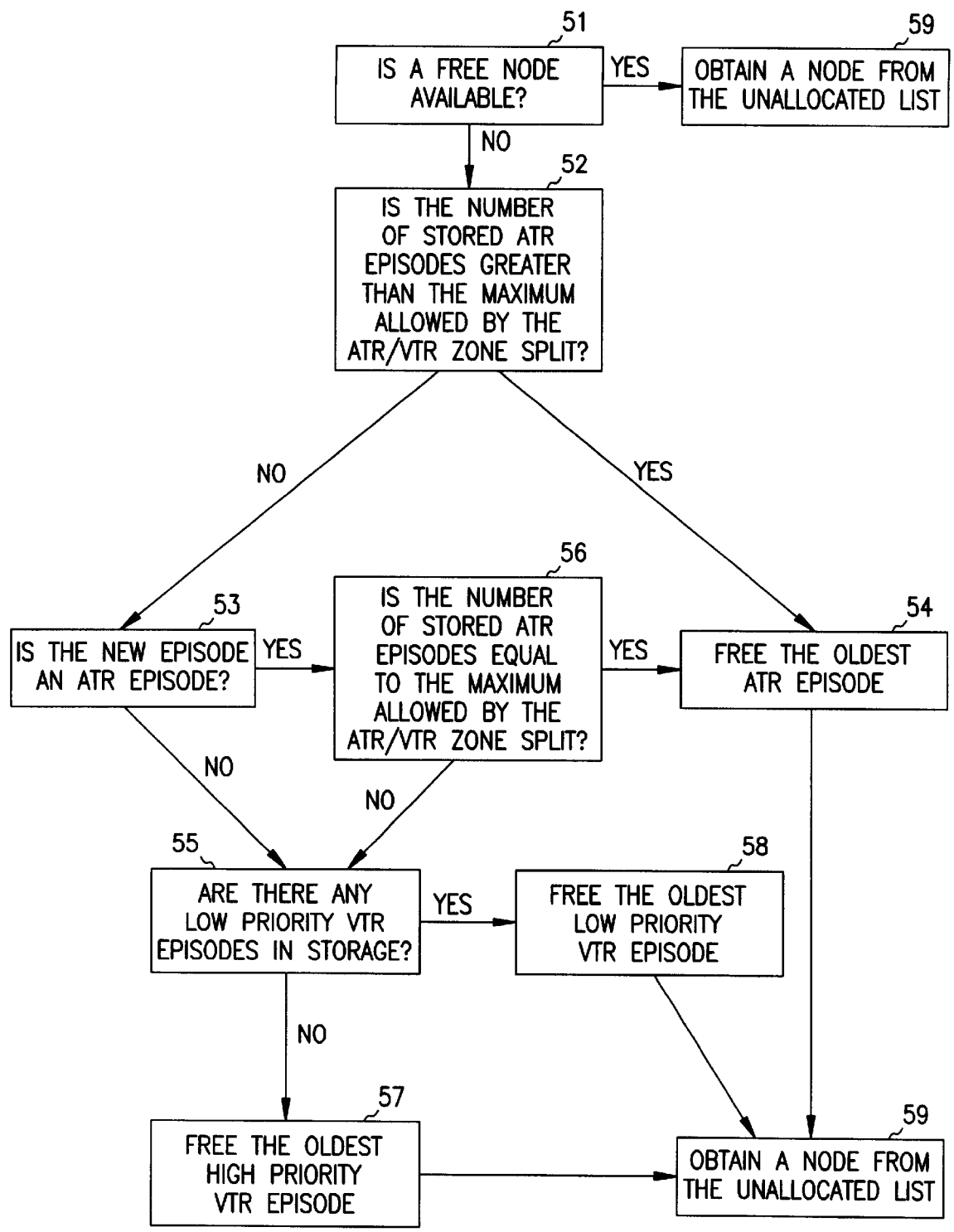
FIG. 3 is a flow chart of a particular decision-making process for freeing previously allocated storage locations.

FIG. 3 shows the decision-making process used to determine which history storage node is used for a new episode. At step 51, the unallocated list is checked and if a node is available, it is allocated to the episode at step 59. If no unallocated node exists, step 52 determines whether the number of ATR episodes is greater than the maximum allowed by the specified ATR/VTR zone split (i.e., the specified maximum number of stored ATR episodes and stored VTR episodes in accordance with the data segmentation scheme). If the specified zone split is already exceeded, it means that there are more stored ATR episodes than are allowed by the specified ATR/VTR zone split, which can happen if the specified split is changed or if the number of ATR episodes crosses the ATR/VTR split boundary before the unallocated list is empty. In that case, the node allocated to the oldest ATR episode is freed at step 54 and allocated to the new episode at step 59. The index of the oldest ATR episode is found in the ATR list head of the history management structure.

If the ATR/VTR zone split is at the specified value or there are more VTR episodes stored than are allowed by the specified zone split, it is next determined whether the new episode is an ATR episode at step 53. If the answer is yes, step 56 determines if the number of stored ATR episodes is equal to the specified allowable maximum (which means that the mix of stored episodes complies with the specified zone split), and if so the oldest ATR episode is replaced with the new ATR episode at steps 54 and 59. If the answer at step 56 is no, there are more VTR episodes in memory than are allowed by the specified zone split, and a VTR episode must be freed. A VTR episode isfalso freed if it is determined at step 53 that the new episode is a VTR episode.

Before freeing a VTR episode, step 55 determines whether there are any low priority VTR episodes in storage. If so, the oldest VTR episode is freed at step 58, with the index of the oldest low priority VTR episode being found in the low priority VTR list head of the history management structure. Step 59, as before, then allocates the newly freed node to new episode. If there are no low priority VTR episodes in storage, the oldest high priority VTR episode is freed at step 57, with the index of the oldest high priority episode being found in the high priority VTR list head of the history management structure, and allocated to the new episode at step 59.

When an episode history storage node is freed, the associated history management structure node allocated to the same episode is also freed, as well as all attempt history storage nodes, interval data storage blocks, and electrogram data storage blocks associated with that episode. If an attempt history storage node is freed, all electrogram data storage blocks associated with the attempt are also freed.

Obtaining free interval data storage blocks and electrogram data storage blocks employs the same logic as obtaining free history storage nodes. When an interval data storage block is freed, all interval data storage blocks associated with an episode are freed. When an electrogram data storage block is freed, all electrogram data storage blocks associated with an electrogram strip are freed.

Once episode data has been retrieved from the device, it is no longer necessary to have the data protected. Therefore, the system preferably provides a method of unprotecting data on command from a telemetry device so that all high priority VTR episodes can placed in the low priority VTR episode list. The chronological order of the episodes is maintained when the data is moved.

What is claimed is:

1. A system for storing episodic data collected by an implantable medical device, comprising:

a history storage structure comprising an array of nodes and wherein data associated with an episode is stored by allocating a history storage node to the episode;

a linked list of unallocated history storage nodes;

a priority type linked list of history storage nodes for each one of a plurality of types of episodes, wherein episodes are classified as being one of a plurality of priority types going from lower to higher; and, wherein a history storage node is allocated to a new episode from the list of unallocated history storage nodes unless the unallocated list is empty, in which case the oldest node from one of the priority type lists is freed for allocation to the new episode.

2. The system of claim 1 wherein history storage nodes are freed from priority type lists and allocated to new episodes according to priority unless a specified maximum number of stored episodes of one particular type would be exceeded by the allocation.

3. The system of claim 1 wherein history storage nodes are freed from lower priority type lists in preference to higher priority type lists in order to allocate a previously allocated node to a new episode.

4. The system of claim 1 further comprising:

a history management structure comprising an array of nodes, wherein for each history storage node allocated to an episode, a history management node is also allocated to the episode and associated with the allocated history storage node;

wherein each allocated history management node has a storage link field that points to the history storage node associated therewith; and, wherein the priority type linked lists of history storage nodes are formed by linking associated history management nodes with each allocated history management node having a link field pointing to an adjacent node in a priority type linked list of history management nodes.

5. The system of claim 4 wherein the priority type linked lists are doubly linked lists with each allocated history management node having link fields pointing to adjacent nodes in both directions.

6. The system of claim 5 further comprising a doubly linked list of all allocated history management nodes with each allocated node having link fields pointing to adjacent nodes in both directions in the all allocated node list.

7. The system of claim 6 wherein the nodes of the priority type linked lists and the all allocated linked list are linked sequentially in accordance with when the episodes to which the nodes are allocated occurred.

8. The system of claim 7 further comprising:
a data storage structure comprising an array of nodes, wherein for each history storage and history management node allocated to an episode, a data storage node is also allocated to the episode and associated with the allocated history storage and history management node;
wherein each allocated history storage node has a link field pointing to an associated data storage node; and,
wherein each data storage node references a data storage block in which episodic data is stored.

9. The system of claim 8 wherein episodic data may be stored in a plurality of data storage blocks referenced by a linked list of data storage nodes allocated to the episode with each allocated data storage node having a link field for pointing to an adjacent data storage node in the linked list.

10. The system of claim 9 wherein the history management structure comprises nodes designated as list heads for the unallocated linked list, the all allocated linked list, and the priority type linked lists.

11. The system of claim 10 wherein each history management node designated as a list head has link fields for pointing to adjacent nodes in both directions.

12. The system of claim 11:
wherein episodic data collected before and after a therapy attempt associated with an episode may be stored in a plurality of data storage blocks referenced by a linked list of data storage nodes allocated to storing data collected before and after the attempt;
wherein a history storage node allocated to an episode has a link field that may reference a history storage node allocated to a therapy attempt associated with the episode; and,
wherein a history storage node allocated to an attempt has a data field in which is stored a value indicating that the node is allocated to an attempt, a link field that references a data storage node allocated to storing data collected before the therapy attempt, and a link field that references a data storage node allocated to storing data collected after the therapy attempt.

13. The system of claim 12 wherein a history storage node allocated to an attempt has a link field that references history storage nodes allocated to any subsequent attempts.

14. The system of claim 1 wherein cardiac electrogram data collected prior to onset of an episode is stored in one or more data storage blocks referenced by a history storage node allocated to the episode.

15. The system of claim 1 wherein cardiac interval data and electrogram data collected after onset of an episode is stored in one or more data storage blocks referenced by a history storage node allocated to the episode.

16. The system of claim 1 wherein cardiac electrogram data collected after onset of an episode is stored in one or more data storage blocks referenced by a history storage node allocated to the episode.

17. The system of claim 11 wherein cardiac electrogram data collected before and after a therapy attempt associated with an episode is stored in one or more data storage blocks referenced by a history storage node allocated to the episode.

18. The system of claim 11 wherein the priority types of episodes stored include an atrial tachyarrhythmia response, a low priority ventricular tachyarrhythmia response, and a high priority ventricular tachyarrhythmia response.

19. The system of claim 11 wherein when a history storage node allocated to an episode is freed, the history management node allocated to the episode, all history storage nodes allocated to therapy attempts associated with the episode, and all data storage nodes and blocks allocated to the episode or associated attempts are also freed.

20. The system of claim 11 wherein a history storage node is allocated to a new therapy attempt associated with an episode from the list of unallocated history storage nodes unless the unallocated list is empty, in which case the oldest node from one of the priority type lists is freed and added to the unallocated list for allocation to the new episode, and wherein the freed node is taken from a lower priority list in preference to a higher priority list unless a specified maximum number of stored episodes of one particular type would then be exceeded.

21. The system of claim 11 wherein a data storage node and the data storage block referenced thereby are allocated to a present episode from the list of unallocated data storage nodes unless the unallocated list is empty, in which case a data storage node allocated to the oldest episode in one of the priority type lists is freed and added to the unallocated list for allocation to the present episode, and wherein the oldest episode is taken from a lower priority list in preference to a higher priority list.

22. A method for storing episodic data collected by an implantable medical device, comprising:
maintaining a linked list of unallocated data storage nodes, wherein each data storage node references a location for storing collected data;
allocating a data storage node from the unallocated list to each episode for which collected data is to be stored;
maintaining a priority type linked list corresponding to each one of a plurality of episode priority types, wherein each priority type linked list comprises data storage nodes allocated to episodes of a particular type linked in an order that corresponds to when the episodes occurred; and,
freeing previously allocated data storage nodes for allocation to a present episode when the unallocated list is empty by freeing the oldest data storage node from one of the priority type lists.

23. The method of claim 22 wherein data storage nodes are freed from priority type lists according to priority unless a specified maximum number of stored episodes of one particular type would then be exceeded.

24. The method of claim 22 wherein the freed previously allocated node for is taken from a lower priority list in preference to a higher priority list.

25. The method of claim 24 further comprising allocating a data storage block to a therapy attempt associated with an episode.

26. The method of claim 25 further comprising storing data collected prior to onset of the episode in a location referenced by the data storage node allocated to the episode.

27. The method of claim 25 further comprising storing data collected before and after the therapy attempt in locations referenced by the data storage node allocated to the attempt.

28. A processor-readable storage medium having processor-executable instructions for performing the method recited in claim 22.

* * * * *